United States Patent [19]

Lider et al.

[11] Patent Number: Plant 6,319

[45] Date of Patent: Oct. 4, 1988

[54] HYBRID GRAPEVINE ROOTSTOCK NAMED 'VR 043-43'

[75] Inventors: Lloyd A. Lider; Harold P. Olmo, both of Davis; Austin C. Goheen, Winters, all of Calif.

[73] Assignee: The Regents of the University of California, Berkeley, Calif.

[21] Appl. No.: 866,537

[22] Filed: May 23, 1986

[51] Int. Cl.[4] ..... A01H 5/03

[52] U.S. Cl. ..... Plt./47

[58] Field of Search ..... Plt./47

*Primary Examiner*—Robert E. Bagwill

*Attorney, Agent, or Firm*—Townsend and Townsend

[57] ABSTRACT

A new and distinct variety of grapevine rootstock is provided. It is characterized by its immunity to feeding by the nematode vector of grapevine fanleaf virus, and when grafted with cultivars, such as 'Cabernet Sauvignon,' 'Chenin blanc,' and 'Carignane,' may be planted in soil contaminated with viruliferous nematodes, producing healthy fruit and excellent yields.

2 Drawing Sheets

The present invention relates to a new and distinct rootstock variety of grapevine. More particularly the new variety, which has been named 'VR 043-43,' has been shown to effectively tolerate grapevine fanleaf virus and *Xiphinema index,* the nematode vector.

Figure 1:
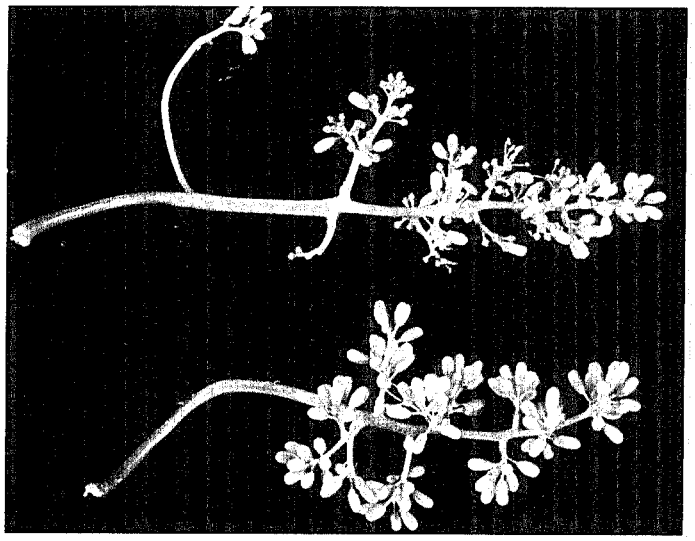

FIG. 1 shows a typical flower cluster form of the new variety.

Figure 2:
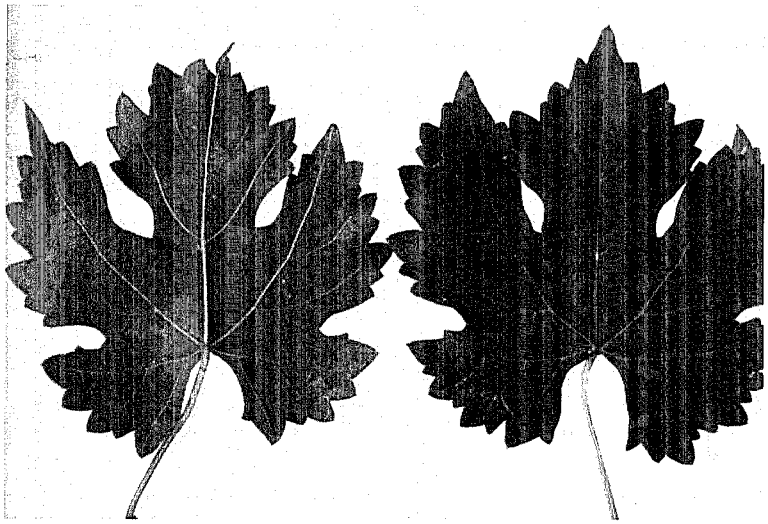

FIG. 2 typifies the mature leaves of the new variety.

Figure 3:
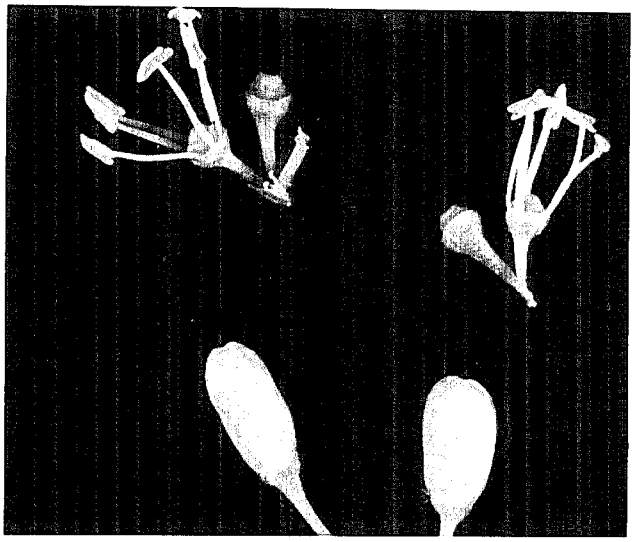

FIG. 3 shows the flowers of the new variety.

A serious problem which has faced the California grape industry for many years is the grapevine fanleaf virus — *Xiphinema index* nematode complex. Soil fumigation treatments have had limited success in controlling the vector spreading infectious degeneration. Frequently soil treatment has completely failed. When planted in soil infested with viruliferous *X. index, Vitis vinifera* grape cultivars become infected with the disease, and vines degenerate rapidly to a point where fruit set is reduced and crop production becomes twenty percent (20%) or less than that of normal healthy vines of the same cultivar.

When *vinifera* scions are grafted onto standard phylloxera resistant rootstocks that are in general use such as 'Harmony,' 'Couderc 1613,' 'Rupestris St. George' ('du Lot') and 'Ganzin 1', degeneration has not been prevented and oftentimes is exacerbated to a point where vines are virtually cropless.

The grapevine of this invention was selected from a cross made in 1948 between *Vitis vinifera* 'Hunisa' and *V. rotundifolia* male No. 2. Initially, the selection was tested for phylloxera resistance and the success of those tests was reported in 1964. However, due to difficulty in propagating the selection as compared with the standard phylloxera-resistant rootstocks, 'VR 043-43' was not released. Interest in this vine was renewed when differential tolerance to infectious degeneration and *X. index* was observed. These observations led to the experiments which have determined the immunity of 'VR 043-43' to *X. index* feeding. Vines of 'VR 043-43,' when grafted with scions of susceptible *vinifera* cultivars such as 'Cabernet Sauvignon,' 'Chenin blanc,' and 'Carignane' and planted in infested soil have remained disease free and productive for at least seven (7) years. The tests were aided by a new serological technique which permits rapid detection of grapevine fanleaf virus in grapevine tissues. The technique is known as enzyme-linked immunosorbent assay (ELISA). ELISA of tissues taken from experimental vines of 'VR 043-43' at various stages of growth gave proof that 'VR 043-43' was virtually free of infectious degeneration. Throughout the extended test period crop yield and vine growth were excellent, and the clusters and berries obtained on 'VR 043-43' stock demonstrated complete freedom of virus infection. The scions on the standard phylloxera-resistant rootstocks in the same tests as 'VR 043-43' displayed severe degeneration evidenced by low yields, smaller clusters and berries and reduced pruning weights.

'VR 043-43' was tested and has been found suitable for planting in vineyards infected with viruliferous nematodes in the important wine grape areas of Napa and San Joaquin Counties in Calif. The variety has been asexually reproduced by cuttings, and although difficult to propagate, propagation has been improved by the application of rooting hormones.

In addition to its immunity to nematode feeding 'VR 043-43' is tolerant to phylloxera and most strains of root knot nematodes. It is distinguished from its companion rootstock 'VR 039-16' in that it is not immune but only tolerant to phylloxera. 'VR 043-43' differs from the standard phylloxera resistant rootstocks in that it is somewhat more difficult to propagate, is immune to vector feeding and resistant to feeding by root knot nematodes.

Definitive phenological and morphological characteristics of 'VR 043-43' are as follows:

*Flowers.*—Flowers distinctly staminate with long filaments. Pollen aborted. Ovary indistinct or rudimentary. Flower cluster form small, 4–6 cm long, sterile with no fruit set.

*Leaves.*—Leaves moderately three to five lobed, occasionally almost entire. Inferior and superior sinuses open, narrow. Leaf margin dentate with tendency for irregular arrangement of large acute teeth. Mature leaves with tufted tomentum on the upper surface. Lower surface glabrous. Mature leaf color green. Young leaves and shoot tips light green in color with moderately soft hairs on upper surface and lower surface glabrous.

*Tendrils.*—Tendrils are bifid, occasionally trifid, long and slender, often longer than the leaf blade, glabrous. Discontinuous arrangement of *vinifera* type.

*Stems.*—Immature stems with distinct ridges and, while young, appear distinctly angled. Widely dispersed soft hairs on the shoots. Petioles and immature wood light green in color.

*Mature wood.*—Mature wood tan in color. Bark persistent with distinct lenticels. Nodes with septum.

*Time of bloom.*—Blossoms late, 10 to 12 days later than Semillon. 10% bloom at Davis on May 23, 1985.

We claim:

1. The new and distinct variety of grapevine rootstock herein described and illustrated and identified by the characteristics enumerated above.

* * * * *